US006425858B1

(12) United States Patent
Minami

(10) Patent No.: US 6,425,858 B1
(45) Date of Patent: Jul. 30, 2002

(54) ELECTRONIC ENDOSCOPE APPARATUS HAVING MAGNIFICATION CHANGING FUNCTION

(75) Inventor: Itsuji Minami, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/526,874

(22) Filed: Mar. 16, 2000

(30) Foreign Application Priority Data

Mar. 19, 1999 (JP) .......................................... 11-075262
Mar. 19, 1999 (JP) .......................................... 11-075263
Mar. 26, 1999 (JP) .......................................... 11-083369

(51) Int. Cl.[7] ................................................ A61B 1/04
(52) U.S. Cl. ......................... 600/168; 600/180; 348/65; 348/68; 348/240; 348/296
(58) Field of Search ................................. 600/109, 160, 600/168, 178, 180–181; 348/65, 68, 69, 240, 296, 358

(56) References Cited

U.S. PATENT DOCUMENTS 4,791,480 A * 12/1988 Muranaka .................... 600/109
5,420,632 A * 5/1995 Yamagiwa .................... 348/358
5,905,530 A * 5/1999 Yokota et al. ................ 348/358
6,046,770 A * 4/2000 Uemura et al. ............... 348/358

FOREIGN PATENT DOCUMENTS

JP 04-233874 * 8/1992 .......... H04N/5/232

* cited by examiner

Primary Examiner—John Mulcahy
(74) Attorney, Agent, or Firm—Ronald R. Snider; Snider & Associates

(57) ABSTRACT

The present invention provides an electronic endoscope apparatus which prevents a picked up image from being blurred utilizing an optical magnification change mechanism. A viewing distance is changed by moving a movable lens with an actuator, magnification changing location of the movable lens is detected with an encoder and a shutter speed for a CCD which is shorter than an exposure time while the optical magnification changing mechanism is not operating is set with a CPU dependently on the magnification changing location. It is possible to prevent an image from being blurred, for example, by storing various patterns which provide higher electronic shutter speeds as an image magnification ratio is enhanced in a ROM and controlling an electronic shutter speed with these patterns. Furthermore, a variable width of a stop is limited to a predetermined width as the electronic shutter speed is enhanced and a gain of a video signal is enhanced with an AGC circuit when image brightness is insufficient due to limitation of a variable width of the stop. When an electronic magnification changing circuit is provided, a displacement speed of optical magnification change is detected on the basis of magnification changing data detected with the encoder, and control is performed at the same speed as this speed so that a shift is made to an electronic magnification changing operation.

9 Claims, 15 Drawing Sheets

ELECTRONIC ENDOSCOPE APPARATUS HAVING MAGNIFICATION CHANGING FUNCTION

BACKGROUND OF THE INVENTION

This application claims the priority of Japanese Patent Application Nos. 11-75262, 11-75263, filed on Mar. 19, 1999, No. 11-83369 filed on Mar. 26, 1999, which are incorporated herein by reference.

1. Field of the Invention

The present invention relates to an electronic endoscope apparatus and more specifically a configuration of an apparatus which picks up an image of an object to be observed with a solid-state image pickup device by utilizing a magnification changing function to change a viewing distance.

2. Description of the Invention

It has recently been proposed to build a magnification changing drive mechanism for changing a viewing distance, for example, in an insertion tip section of an endoscope and drive a movable lens which is a component member of the magnification changing mechanism. The magnification changing mechanism transmits a rotating drive force of a motor to a magnification changing mechanism section using a linear transmitting member, for example, a multiply coiled spring, which converts a rotating motion into a linear motion to move a predetermined movable lens of an objective optical system frontward and rearward, thereby carrying out a magnification changing operation using a vari-focal optical system for changing a viewing distance or a zoom optical system for changing a focal length. Such a magnification changing drive mechanism allows observance of a magnified image of an object to be observed, thereby :making it possible to perform delicate diagnoses.

BRIEF SUMMARY OF THE INVENTION

However, an electronic endoscope apparatus which has a magnification changing function described above permits magnifying an image of an interior of the object to be observed and allows observance of a detailed image of a focus on a monitor or the like, but on the other hand, it poses a problem that an image to be observed may be blurred. Speaking more concretely, magnification of the image to be observed means magnification of a blur which is caused due to pulsation of a location to be observed or swinging of the tip section of an inserting stage and little in a standard observing condition; and cannot be ignored when a still image is When the vari-focal optical system is adopted for the magnification changing mechanism to be built in the insertion tip section of an endoscope, it is necessary for focusing after a change of a viewing distance to move the tip section (objective optical system) of the of the endoscope more or less frontward or rearward. Accordingly, an image is liable to be blurred due to the swinging of the tip section as compared with an image in the standard observation mode (without using the magnification changing mechanism).

On the other hand, this kind of endoscope performs automatic light quantity control with a stop mechanism using a stop member or the like to maintain constant image brightness and it is necessary to execute this brightness adjustment in a stable condition even when the magnification changing function described above is used.

Furthermore, a conventional electronic endoscope apparatus has an electronic zoom function to magnify or contract a video signal obtained with a CCD (charge coupled device) which is a solid-state image pickup device. Accordingly, it will be possible to enhance a magnification ratio if this electronic magnification changing function can be combined with an optical magnification changing function described above. In this case, it is demanded not to simply provide the optical magnification changing function and the electronic magnification changing function, but to smoothly switch or change these functions with no strange feeling during a magnification changing operation.

SUMMARY OF THE INVENTION

The present invention has been achieved in view of the problem described above and has a primary object to provide an electronic endoscope apparatus which is capable of preventing an image from being blurred when the image is picked up by utilizing a magnification changing mechanism and obtaining stable brightness of the image.

Furthermore, another object of the present invention is to provide an electronic endoscope apparatus which is capable of enhancing a magnification ratio by combining an optical magnification changing function with an electronic magnification changing function and smoothly switching these two functions during a magnification changing operation.

In order to accomplish the objects described above, an electronic endoscope apparatus having a magnification changing function according to a first invention comprises an optical magnification changing mechanism which is capable of optically magnifying an image to be observed with an objective optical system, a solid-state image pickup device which picks up an image of an object to be observed with rays incident from the objective optical system, and an electronic shutter control circuit which controls an electric charge accumulating time of the solid-state image pickup device and sets a high shutter speed to set an exposure time while the magnification changing mechanism is operative which is shorter than that while the magnification changing mechanism is inoperative.

It is preferable for the electronic endoscope apparatus described above to store in a memory various kinds of patterns of electronic shutter speeds which are enhanced as the optical magnification changing mechanism enhances a image magnification ratio and control the electronic shutter speed by reading out data of a pattern selected from the memory.

When an exposure time of approximately $1/60$ second is set in a standard condition of the configuration according to the first invention, an electronic shutter speed, for example, of $1/500$ second is set for a magnification at a middle point of the magnification changing operation and an electronic shutter speed of $1/10000$ second is set for a maximum magnification. That is, a higher shutter speed is set for a higher magnification ratio and the variable setting of the shutter is performed by controlling pulses to discharge electric charges accumulated by a CCD which is a solid-state image pickup device so as to change an electric charge accumulating time left after discharge. When the plurality of patterns of the electronic shutter speeds are stored in the memory, the electronic shutter speeds can be set dependently on magnification ratios, and selected and used dependently on locations to be observed, observing conditions, observer's demands and so on.

An electronic endoscope apparatus according to a second invention is characterized by comprising not only the optical magnification changing mechanism which optically magnifies an image, the solid-state image pickup device and the electronic shutter control circuit which are described above but also a stop mechanism which variably controls rays output from a light source with a stop member and a control circuit which limits a variable width of the stop mechanism to a predetermined width as the electronic shutter speed is enhanced while the magnification changing mechanism is operative.

The electronic endoscope apparatus described above can comprise a gain control circuit which variably controls a gain of a image signal output from the solid-state image pickup device, thereby being capable of detecting brightness of an image from the video signal with the control circuit and maintaining constant image brightness by controlling the gain of the image signal with the gain control circuit when predetermined brightness cannot be obtained even by the light quantity control with the stop mechanism.

Like the first invention, a configuration, the second invention provides a configuration which varies or controls the shutter speed so as to be higher at a higher magnification ratio by controlling an electric charge accumulating time as a magnification ratio is enhanced. The electronic endoscope apparatus controls the image brightness constant by driving the stop mechanism even during a shutter speed changing operation, but since the shutter speed is set at a high level, the system may allow response of the stop mechanism to be delayed, thereby making the light quantity adjustment unstable and disturbing a screen when the shutter speed is variable within a broad range or when the object to be observed moves abruptly. Therefore, the present invention limits a variable range of the stop mechanism to the predetermined width as the electronic shutter speed is enhanced, thereby preventing the response of the stop mechanism from being delayed and suppressing disturbance of the screen.

On the other hand, a light quantity may be insufficient to obtain definite brightness when the variable amount of the stop mechanism is limited as described above. When brightness is insufficient, the electronic endoscope apparatus according to the second invention therefore controls to enhance the gain of the image signal based on judgement of an image brightness signal such as a luminance signal, thereby maintaining brightness at a constant level by this signal amplification processing.

An electronic endoscope apparatus according to a third invention comprises an optical magnification changing mechanism which is capable of optically magnifying an image to be observed with an objective optical system, a solid-state image pickup device which picks up an image of an object to be observed with rays incident from the objective optical system, an electronic magnification changing circuit which forms a magnified image and contracted image from an image at an operation end of the optical magnification changing mechanism, and a magnification changing speed control circuit which detects a displacement speed of a magnification change in the optical magnification changing mechanism and controls to match this displacement speed with a displacement speed of an electronic magnification change at a switching point between an optical magnification changing operation and an electronic magnification changing operation.

The electronic endoscope apparatus described above is capable of executing the optical magnification changing operation, the electronic magnification changing operation and switching between these operations with a single magnification changing switch.

The configuration according to the third invention is capable of changing a viewing distance from a far position to a near position by driving, for example, a movable lens of the optical magnification changing mechanism and providing an image which is further magnified by operating an electronic magnification changing function after the movable lens reaches the near position. In this case, the electronic endoscope apparatus detects a driven speed of the movable lens, that is, the displacement speed of the magnification change and executes the electronic magnification changing operation at the same displacement speed referring to the displacement speed mentioned above at a stage to shift to the electronic magnification changing operation (also at a stage to return to the optical magnification changing operation). Accordingly, a magnification change of an image can be displayed with no feeling of strangeness even during switching between two functions.

Furthermore, a current electronic shutter speed, a current displacement speed of the optical magnification change and a current optical magnification change or electronic magnification change for an image can be displayed on a monitor.

DETAILED DESCRIPTION OF THE PREFERRED EMBODIMENTS

First Embodiment

Figure 1:
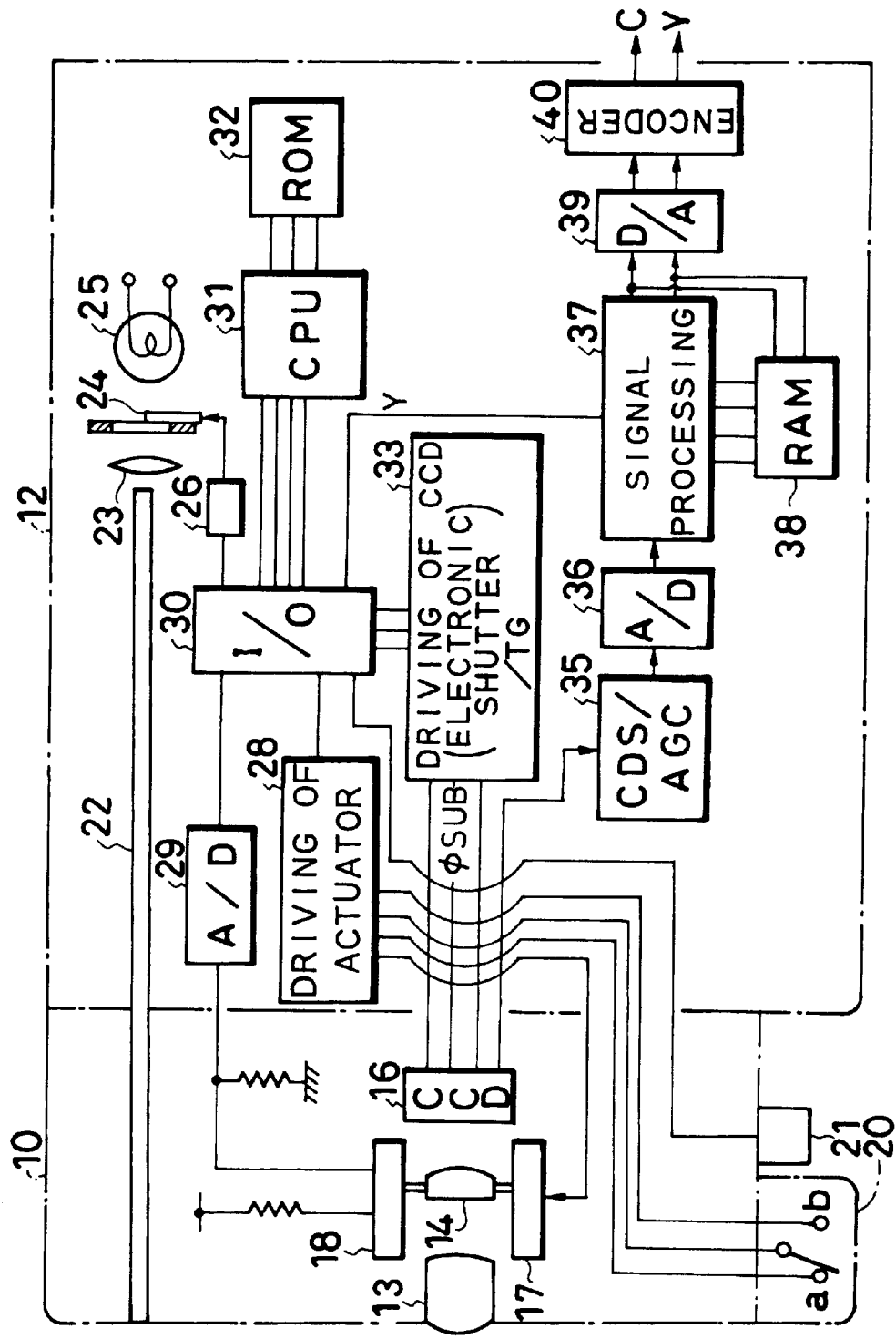
FIG. 1 is a diagram showing an overall configuration of a first embodiment of the electronic endoscope apparatus having the magnification changing function according to the present invention.
Figure 2:
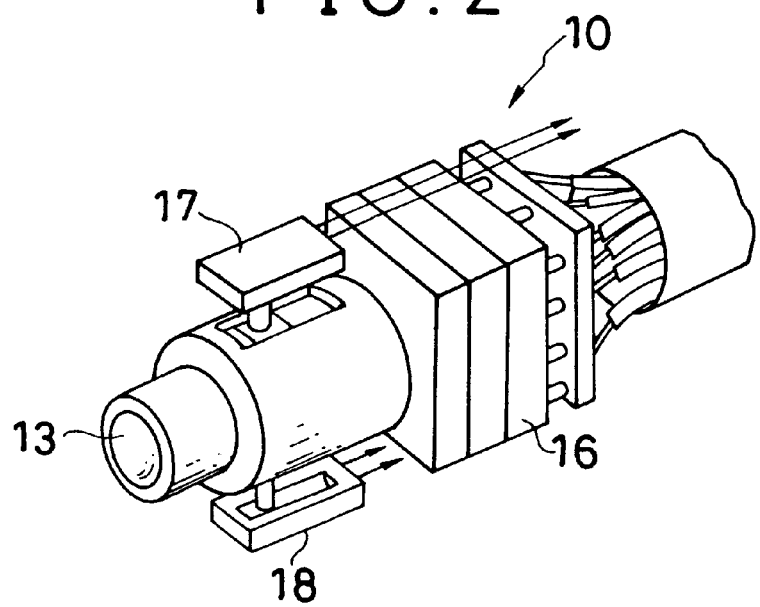
FIG. 2 is a perspective view showing a configuration of an image pickup system of the electronic endoscope apparatus shown in FIG. 1.

FIGS. 1 and 2 show a configuration of a first embodiment of the electronic endoscope apparatus having the magnification changing function according to the present invention, and an electronic endoscope (scope) 10 shown in FIG. 1 is connected to a light source-processor unit 12 via a connector. In the electronic endoscope 10, a front lens 13 and a movable lens 14 are disposed as a vari-focal objective optical system or a zoom objective optical system, and a CCD (charge coupled device) 16 is arranged after the movable lens 14.

A driving actuator 17 and an encoder 18 (or another detector) which detects a driven lens location (magnification changing location) are attached to the movable lens 14 as shown also in FIG. 2 so that a magnification ratio is judged on the basis of an output from the encoder 18. Furthermore, a magnification changing switch 20 consisting of a toggle switch, a seesaw switch or the like and a shutter speed setting switch 21 for manual setting of a shutter speed are disposed, for example, on an operation unit of the electronic endoscope 10, and the magnification changing switch 20 is capable of displacing the movable lens 14 in a magnifying direction and a contracting direction when it is connected to a terminal a and a terminal b respectively. In addition, disposed on the operation unit is a freeze button or the like which is used to form and record a still image and the like.

Furthermore, a light guide 22 is laid from the electronic endoscope 10 to the light source-processor unit 12, a stop 24 is disposed at a light-incidence end of the light guide 22 with a condenser lens 23 interposed, and a light source lamp 25 is arranged after the stop 24. The stop 24 is driven by a stop driving circuit 26 and, as described later in detail, an aperture degree of the stop 24 is controlled to adjust a quantity of output rays, thereby maintaining brightness of an image constant.

An actuator driving circuit 28 which drives the actuator 17 and an AID converter 29 which converts an analog output from the encoder 18 into a digital signal are disposed in the light source-processor until 12, and connected by way of an I/O unit 30 to a CPU 31 which controls circuits collectively. When the magnification changing switch 20 is manipulated, the actuator 17 is operated by the actuator driving circuit 28 to move the movable lens 14 frontward or rearward, whereby the first embodiment changes a viewing distance in a direction toward the far position by moving the movable lens 14 frontward and in a direction toward the near position by moving the movable lens 14 rearward in the vari-focal optical system. In the case of the zoom optical system, a focal length is changed in directions toward a teleposition and a direction toward a wide position by moving the movable lens 14 as described above.

On the other hand, a moved location of the movable lens 14 is detected by the encoder 18 and the location of the movable lens 14 is controlled by giving a detected value to the actuator driving circuit 28 via the A/D converter. An output from the encoder 18 is supplied as a magnification changing location also to the CPU 31 by way of the I/O unit 30 and the CPU 31 outputs an electronic shutter command signal on the basis of the magnification changing location of the movable lens 14.

Figure 3A:
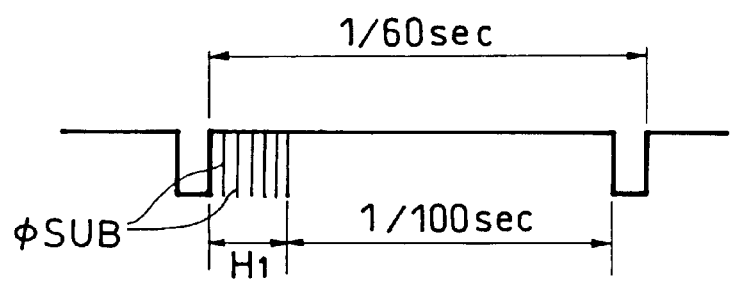
FIGS. 3A and 3B are diagrams descriptive of an example of operations of an electronic shutter in the first embodiment.
Figure 3B:
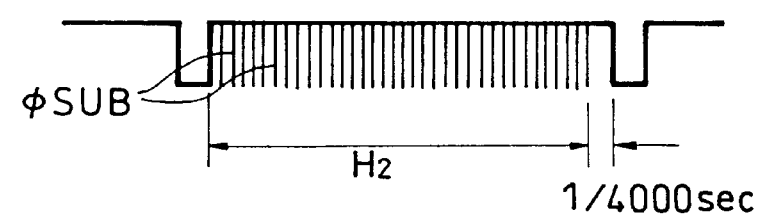

Furthermore, connected to the CCD 16 is a CCD driving circuit 33 comprising a timing generator (TG) which executes drive control of the CCD 16 and electronic shutter control while receiving the command signal from the CPU 31. This electronic shutter control is carried out to change an electric charge accumulating time (exposure time) by adjusting a discharge time of an electric charge accumulating operation of the CCD 16, for example, to set an electric charge accumulating time, that is, a shutter speed as a rest time of $\frac{1}{100}$ second as shown in FIG. 3(A) by outputting discharge pulses $\phi$SUB for a time of H1 which are provided at intervals of 1H (horizontal scanning period) during a vertical scanning period of $\frac{1}{60}$ second as shown in FIGS. 3(A) and 3(B) or a shutter speed of $\frac{1}{4000}$ second by outputting the discharge pulses $\phi$SUB for a time of H2 as shown in FIG. 3(B). Electric charges (an exposure signal) which are accumulated at this shutter speed are read out when a terminal end of a vertical synchronizing signal falls.

Figure 4:
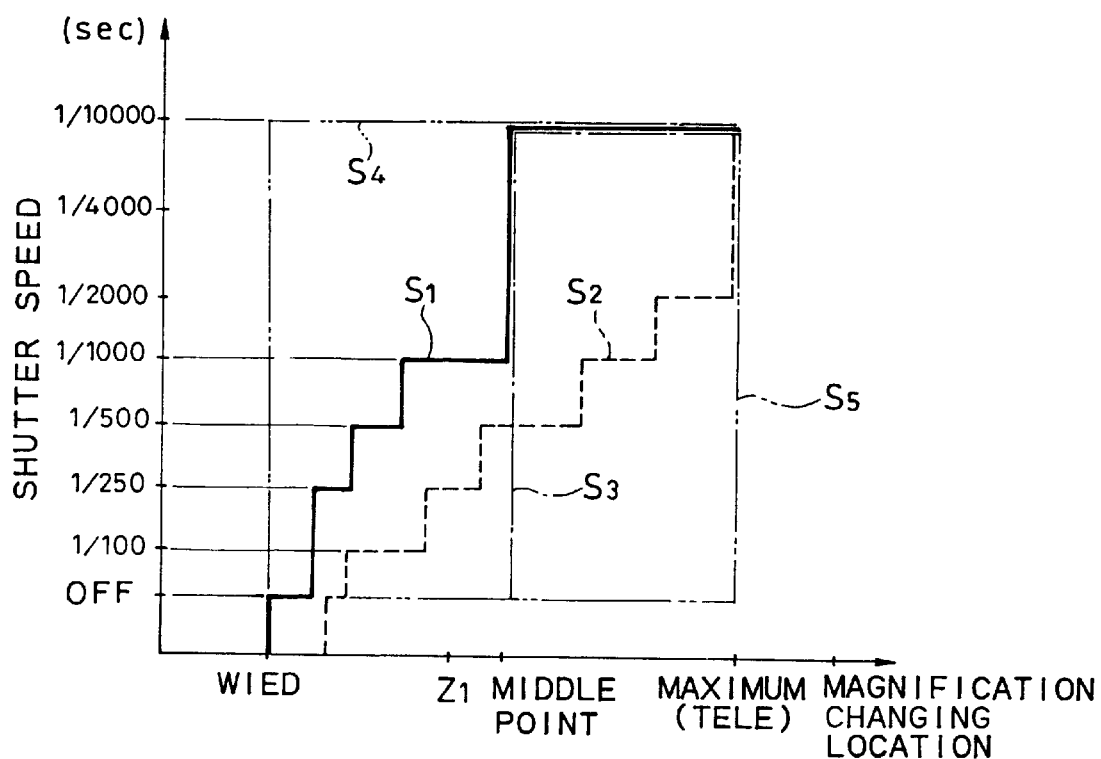
FIG. 4 is a graph showing various patterns to control the electronic shutter in the first embodiment.

The first embodiment is configured to be capable of executing a plurality of control patterns shown in FIG. 4 by the electronic shutter control described above. Speaking concretely, control patterns S1 through S5 are stored in a ROM (read only memory) 32 which is connected to the CPU 31 and can be selected with setting switches arranged on an operation panel (not shown) of the light source-processor unit 12 or settings on a monitor screen. When the pattern S4 is selected, for example, as a simple control example, a shutter speed of $\frac{1}{10000}$ second is set at all magnification changing locations while the movable lens 14 is moved from the wide position toward the tele position.

Figure 5:
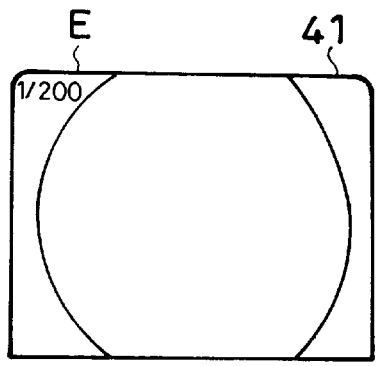
FIG. 5 is a diagram showing a shutter speed display condition on a monitor in the first embodiment.

In order to process a video signal obtained with the CCD 16, on the other hand, there are disposed a CDS (correlated double sampling)/AGC (automatic gain control) circuit 35 which carries out a clamp processing and signal amplification processing, an A/D converter 36, a signal processing circuit 37 which generates a color difference signal C and a luminance signal Y, for example, and carries out various kinds of processings such as gamma correction and contour correction, a RAM (random access memory) 38 which stores data processed by the signal processing circuit 37, a D/A converter 39 and an encoder 40 which processes an output to the monitor and so on. In addition, the first embodiment carries out not only a display processing of an image of an object to be observed but also a display processing of the electronic shutter speed, thereby displaying a set electronic shutter speed at a corner E of the screen, for example, as shown in FIG. 5.

The luminance signal Y obtained with the signal processing circuit 37 is supplied also to the CPU 31, which controls the aperture degree of the stop 24 of the light source by way of the stop driving circuit 26 so that the luminance signal Y has a predetermined value, thereby maintaining brightness of the image (screen) constant. Accordingly, a quantity of output rays is adjusted and brightness of the image is maintained constant even when an exposure time is shortened by the electronic shutter control described above.

The configuration of the first embodiment described above allows rays emitted from the light source lamp 25 shown in FIG. 1 to be projected from the tip of the electronic endoscope 10 by way of the light guide 22, thereby picking up an image of the interior of the object to be observed with the CCD 16 by way of the objective optical system consisting of the lenses 13 and 14. When the magnification changing switch 20 on the operation unit of the electronic endoscope 10 is not manipulated and the movable lens 14 is located at the wide position, the CCD driving circuit does not carry out the electronic shutter control and reads out electric charges which are accumulated for approximately ⅟60 second (this exposure time is optional), for example, after fixed discharge pulses φSUB are output. By processing a read signal as a video signal, the color difference signal C and the luminance signal Y are output from the encoder 40, whereby the image of the object to be observed is displayed on the monitor.

When the magnification changing switch 20 is manipulated, on the other hand, the actuator 17 is driven under control by the actuator driving circuit 28 to move the movable lens 14 frontward from the wide position, thereby magnifying the image. Simultaneously, the encoder 18 detects a magnification changing location (tele position) of the movable lens 14, and a value of a detected location is utilized as a control value by the actuator driving circuit 28 and supplied as current magnification changing data to the CPU 31 by way of the I/O unit 30. On the basis of the control pattern in the ROM 32, the CPU 31 outputs a command signal for an electronic shutter speed corresponding to a current magnification changing location.

When the movable lens 14 is moved to a magnification changing location Z1 before a middle point shown in FIG. 4, for example, a command signal for a shutter speed of ⅟1000 second is output to the CCD driving circuit 33 when the pattern S1 is selected, a command signal for a shutter speed of ⅟250 second is output to the CCD driving circuit 33 when the pattern S2 is selected, a command signal for a shutter speed of ⅟10000 second is output to the CCD driving circuit 33 when the pattern S4 is selected, or a command signal for a shutter speed of approximately ⅟60 second (a time which is the same as that at the wide position when the magnification changing switch 20 is turned OFF) is output to the CCD driving circuit 33 when the pattern S3 or S5 is selected. The CCD driving circuit 33 controls the output of the discharge pulses φSUB (time H) as described with reference to FIGS. 3(A) and 3(B), thereby setting the electronic shutter speed described above. A value of this electronic shutter speed is displayed at the corner E of a monitor 41 as shown in FIG. 5.

When the image is magnified by manipulating the magnification changing switch 20 as described above, a high electronic shutter speed is selected and the image of the interior of the object to be observed is formed by exposing the interior to the CCD 16 for a short time, whereby a favorable image is formed by preventing a magnified image from being blurred even if the tip of the electronic endoscope 10 is swung or a location to be observed pulsates and a still image which is not blurred is displayed even when the freeze button is manipulated.

Furthermore, favorable brightness of the image is not lowered by enhancing the electronic shutter speed since the CPU 31 controls the quantity of rays coming through the stop 24 on the basis of the luminance signal Y and by way of the stop driving circuit 26 as described above. Though the image may be darkened by enhancing the electronic shutter speed when the electronic endoscope apparatus uses the zoom optical system, this problem can be solved by adopting a control pattern which limits a maximum shutter speed, for example, on the order of ⅟500 second.

Figure 11:
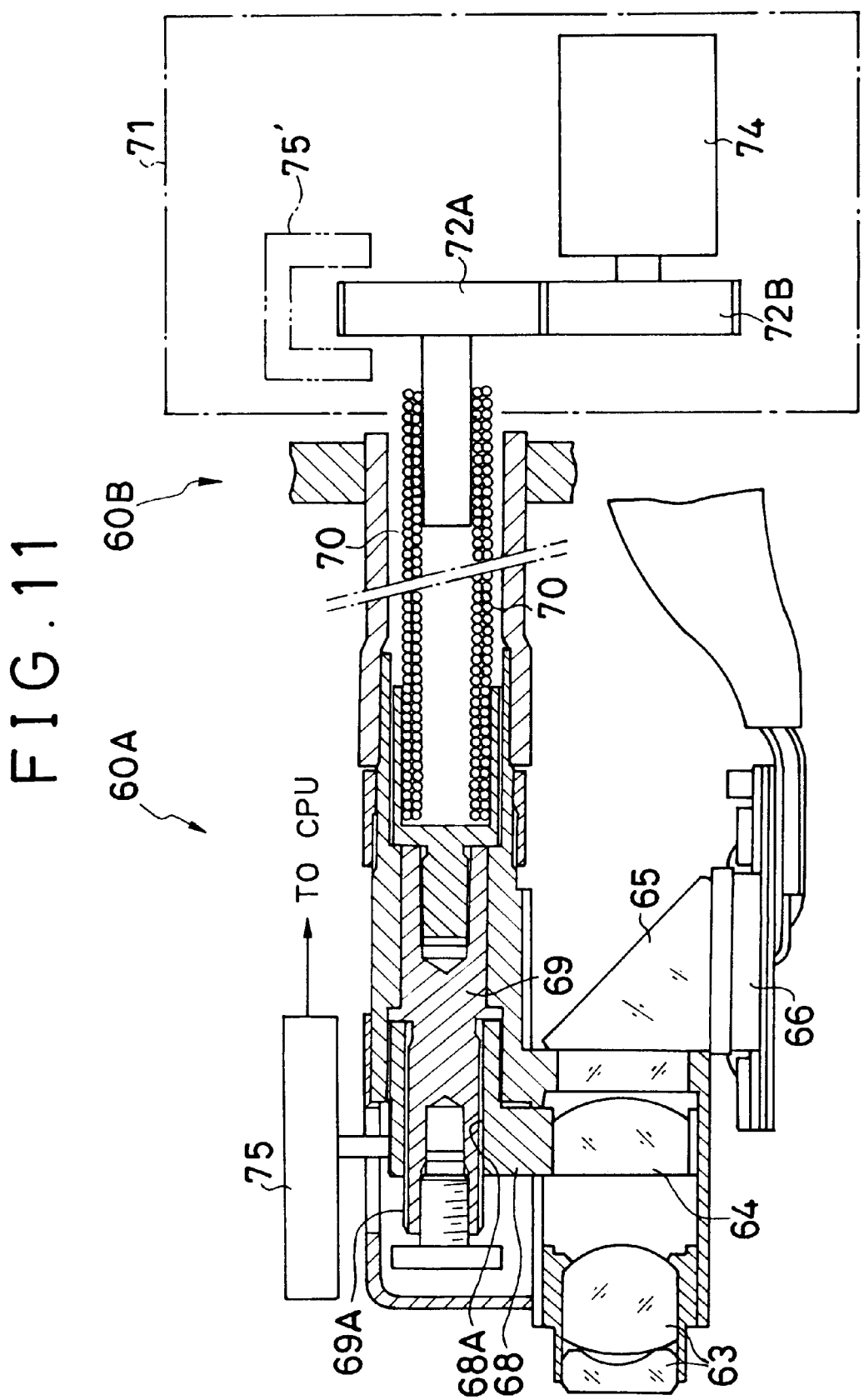
FIG. 11 is a partial sectional view showing an optical magnification changing mechanism of the electronic endoscope apparatus shown in FIG. 10.

Though the movable lens 14 is driven with the actuator 17 in the first embodiment described above, it is possible to utilize a magnification changing drive mechanism which uses a linear transmission member of a third embodiment shown in FIG. 11. This magnification changing drive mechanism allows a motor 74 shown in FIG. 11 to be rotated by manipulating the magnification changing switch 20 shown in FIG. 1, and moves the movable lens 14 frontward and rearward by screw coupling between a rotating drive body 60 at a tip of a linear transmission member 70 and a holding member 68, thereby Carrying out a magnification changing operation. A driven location of the movable lens 14 is detected with an encoder 40 and a detected value is supplied to the CPU 31 to execute an acceleration control of an electronic shutter speed like that described above, thereby preventing an image from being blurred.

Though the encoder 18 is used in the first embodiment described above, it is possible to control the electronic shutter using in place of the encoder detecting means which detects only whether or not the movable lens 14 is located at the wide position, that is, a start end of the magnification changing operation (near position) or a terminal end of the magnification changing operation (far position). For example, the pattern S4 shown in FIG. 4 can be executed upon detection of a movement of the movable lens 14 from the start end and the pattern S5 can be executed upon detection of arrival at the terminal end.

Furthermore, the first embodiment allows a user to manually set an electronic shutter speed since the first embodiment comprises the shutter speed setting switch 21 which is disposed for manual setting of the shutter speed as described with reference to FIG. 1. When the setting switch 21 is configured to cyclically change a value each time it is depressed, for example, it is possible to set the shutter speed of the pattern S4 or S5 described above at a desired speed while confirming the display (E) on the screen 41.

Though the present invention is applied with no discrimination between a moving image and a still image in the first embodiment described above, it is possible to apply the electronic shutter control according to the present invention only when a still image is to be formed. It is possible, for example, not to accelerate the electronic shutter even when the magnification changing mechanism operates to form a moving image but to perform acceleration control of the electronic shutter only when the freeze button is depressed while the magnification changing mechanism is operating.

The first embodiment permits selecting electronic shutter speeds dependently on locations to be observed, observing conditions and observer's demands as described above, and is capable of preventing an image from being blurred when the image is picked up utilizing the magnification changing mechanism, thereby making it possible to obtain a favorable image as described above.

Second Embodiment

Figure 6:
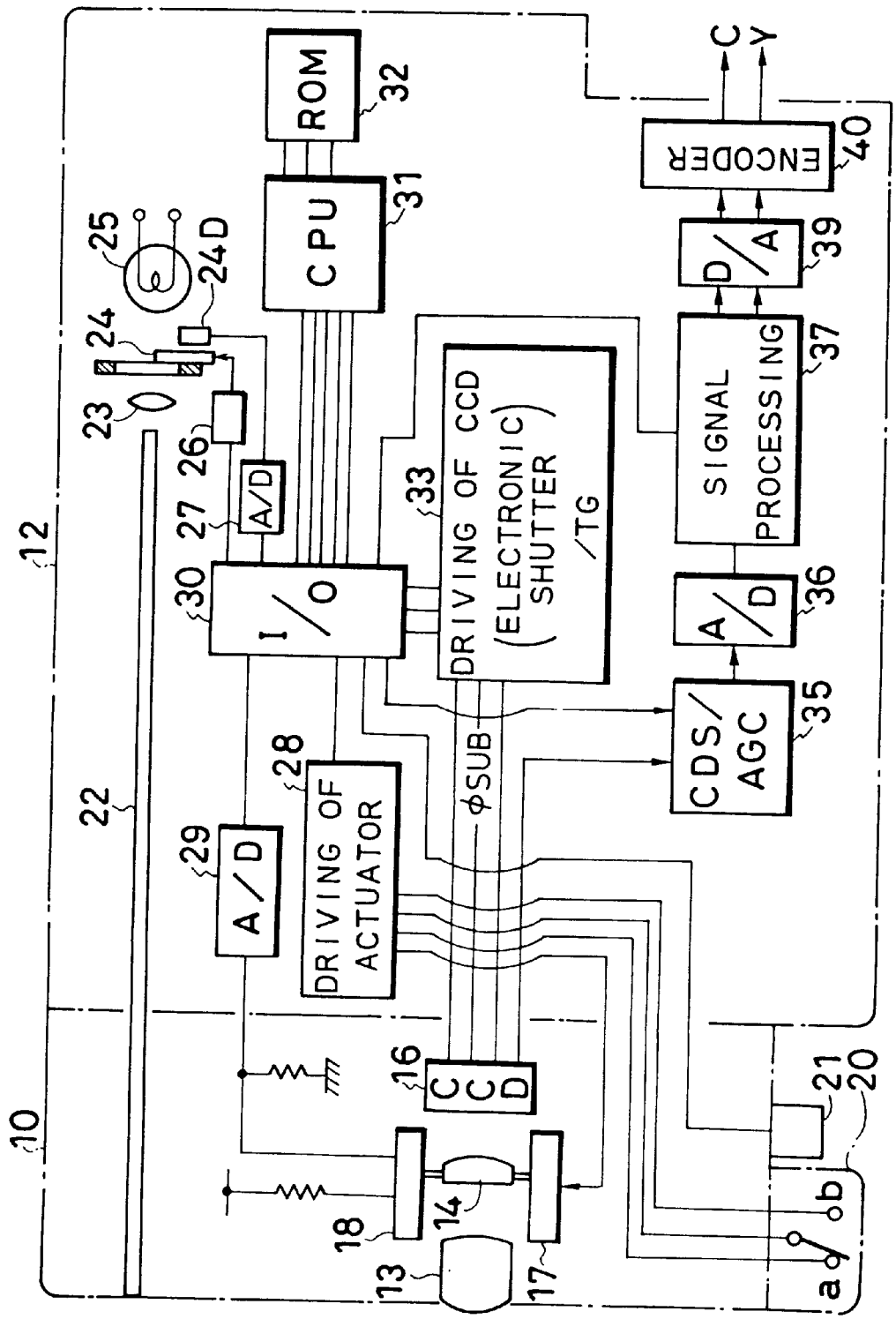
FIG. 6 is a diagram showing an overall configuration of a second embodiment of the electronic endoscope apparatus having the magnification changing function according to the present invention.

FIG. 6 shows a configuration of a second embodiment of 10 the electronic endoscope apparatus having the magnification changing function which has a basic circuit composition similar to that shown in FIG. 1. As shown in FIG. 2, a driving actuator 17 and an encoder 18 which detects a driven lens location are attached to a movable lens 14 shown in FIG. 6. Furthermore, a stop 24 disposed in a light source section of a processor unit 12 is driven with a stop driving circuit 26 and brightness of an image is maintained constant by controlling an aperture degree of the stop 24 on the basis of a luminance signal or the like. One of stop 24 positions (driven positions) ranging from a fully open position to a fully closed position is detected with a stop position detector (encoder or the like) 24D and a detected value is converted into a digital signal by an A/D converter 27.

Figure 7:
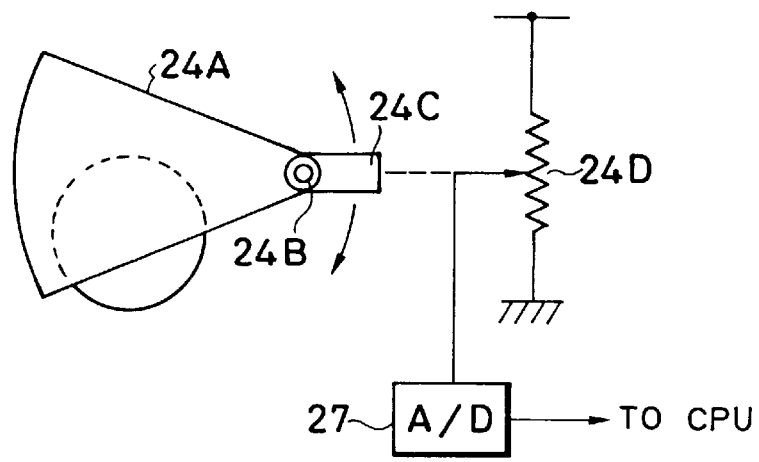
FIG. 7 is a diagram showing a configuration consisting of a stop mechanism and a stop position detector in the second embodiment.

FIG. 7 shows a configuration consisting of the stop 24 and the position detector 24D, wherein the stop 24 has a stop blade 24A which has a sectorial shape, for example, and rotates around a shaft 24B, whereas the stop position detector 24D is capable of detecting a rotating condition of a root 24C of the blade 24A as a voltage change and outputting a stop position which is a rotating position to the A/D converter 27 as a detected voltage value.

When a magnification changing switch 20 on an electronic endoscope 10 is manipulated, the light source-processor unit 12 is capable of moving the movable lens 14 frontward and rearward by operating the actuator 17 by way of an actuator driving circuit 28, thereby changing a viewing distance (focal length) in the direction toward the far position by moving the movable lens 14 front ward and in the direction toward the near position by moving the movable lens 14 rearward.

By giving a value detected with the encoder 18 to the actuator driving circuit 28 by way of the A/D converter 29, on the other hand, a location of the movable lens 14 is controlled and a CPU 31 outputs a command signal for an electronic shutter speed on the basis of a magnification changing location of the movable lens 14. Furthermore, there is disposed a CCD driving circuit 33 comprising a timing generator (TG) which receives the command signal from the CPU 31 and executes electronic shutter control. Since discharge pulses $\phi$SUB are output at intervals of 1H (a horizontal scanning period) during a vertical scanning period of $\frac{1}{60}$ second, for example, as described with reference to FIG. 3, an optional electric charge accumulating time, that is, an electronic shutter speed is set by controlling outputs of the discharge pulses $\phi$SUB.

Figure 8:
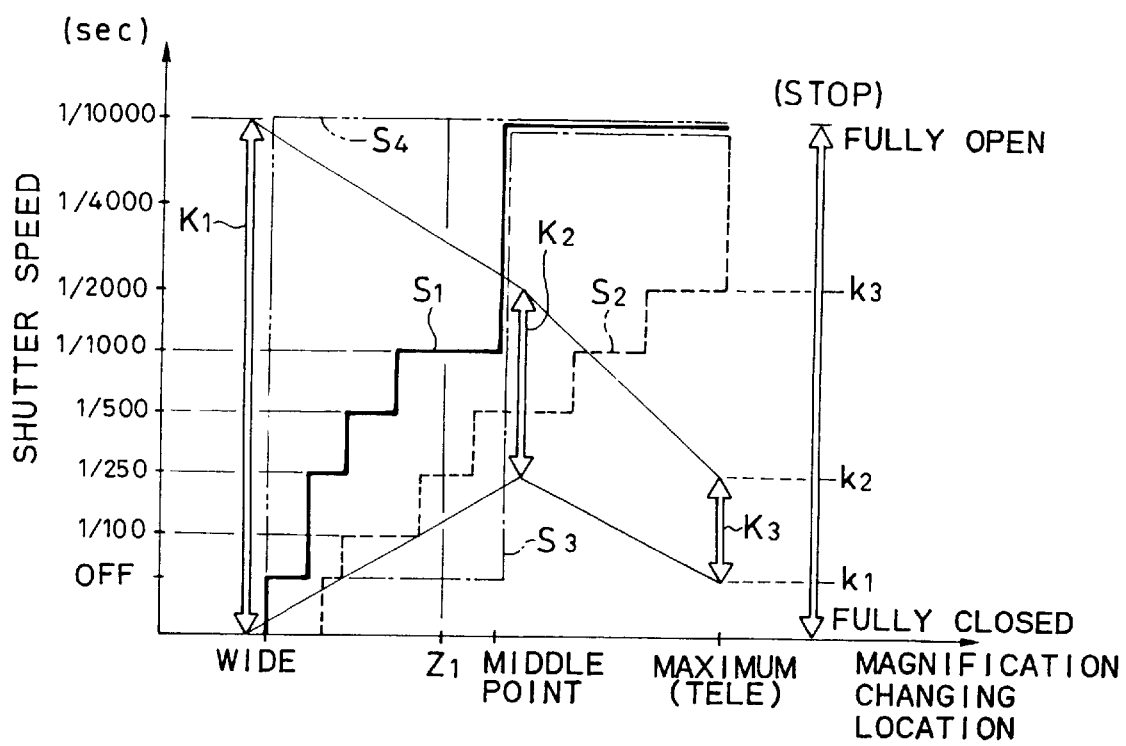
FIG. 8 is a graph showing various patterns to control an electronic shutter and a variable width of a stop in the second embodiment.

The second embodiment is capable of executing a plurality of control patterns shown in FIG. 8 by the electronic shutter control. In other words, control patterns (tables) S1 to S4 shown in FIG. 8, for example, are stored in a ROM 32 shown in FIG. 6 and one of these patterns can be selected with a setting switch or the like.

In order to process a video signal obtained with a CCD 16, there are disposed a CDS/AGC circuit 35, a signal processing circuit 37 which generates a color difference signal C and a luminance signal Y, for example, and performs various kinds of processings, an encoder 40 or the like. A processing to display the electronic shutter speed is carried out together with a processing to display an image of an object to be observed as shown in FIG. 5.

Furthermore, the CPU 31 controls an aperture degree of the stop 24 by way of the stop driving circuit 26 so that the luminance signal Y obtained with the signal processing circuit 37 has a predetermined value, thereby maintaining brightness of a screen constant. Accordingly, a quantity of output rays is adjusted and the b:rightness of an image is maintained constant even when an exposure time is shortened by the electronic shutter control.

The second embodiments limits a variable width of the stop 24 to a predetermined width while a magnification changing mechanism is operating. Speaking concretely, a usable range is limited, for example, to a width K2 (between stop positions k2 and k3) at a middle magnification changing location and a width K3 (between stop positions k1 and k2) at a maximum magnification changing location though an entire range of a width K1 is usable when an aperture degree is taken as an ordinate, and its lowermost and uppermost ends are taken as a fully closed position and a fully open position respectively as shown in FIG. 8. A variable width K is set so as to be basically narrower as an image magnification ratio is enhanced and a higher electronic shutter speed is set. This setting makes it possible to prevent response of a stop mechanism (24) from being delayed by enhancing the electronic shutter speed. Limiting data (tables) for the stop 24 is stored in the ROM 32 together with patterns of electronic shutter speeds so that the electronic shutter speed is controlled by reading the limiting data out of the ROM 32.

When a vari-focal optical system such as that described above is used as a lens system of the magnification changing mechanism in the second embodiment in particular, it is necessary to more or less move the tip of the endoscope for focusing at a magnification changing operation time and the tip of the endoscope is moved slightly frontward to enhance a magnification ratio. Accordingly, a tip of the light guide is also moved frontward and a quantity of rays which irradiate the object to be observed tends to be increased, whereby it is not necessary so often to remarkably control a quantity of rays with the stop 24. Therefore, brightness of an image is rarely changed extremely by limiting the variable width of the stop 24 as described above.

However, the brightness of the image is not always sufficient. The CPU 31 used in the second embodiment therefore controls an automatic gain control circuit of the CDS/AGC circuit 35 so as to enhance a gain of an image signal (video signal) when the CPU 31 judges that a quantity of rays is insufficient on the basis of the luminance signal or the like. As a result, the brightness of the image is always maintained constant.

The configuration of the second embodiment allows rays emitted from the light source lamp 25 shown in FIG. 6 to be projected from the tip of the endoscope, thereby allowing the CCD 16 to pick up an image of the interior of the object to be observed by way of the objective optical system consisting of the lenses 13 and 14. When the magnification changing switch 20 is not manipulated, the second embodiment does not perform the electronic shutter control and limitation of the variable width of the stop mechanism, reads out electric charges accumulated for a time of approximately $\frac{1}{60}$ second, and generates the color difference signal C and the luminance signal Y from a read signal, thereby displaying an image of the interior of the object to be observed.

When the magnification changing switch 20 is manipulated, on the other hand, the second embodiment drives the actuator 17 to move the movable lens 14 frontward from the wide position, thereby magnifying an image. Simultaneously, the encoder 18 detects a magnification changing location (tele position) of the movable lens 14 and supplies a detected value of the location as a current magnification changing location to the CPU 31 by way of the I/O unit 30. The CPU 31 outputs a command signal for an electronic shutter speed corresponding to the current magnification changing location on the basis of the control pattern in the ROM 32. When the movable lens 14 is moved to a magnification changing location Z1 before a middle point in FIG. 8, for example, and the pattern S1 is selected, the CPU 31 outputs a command signal for an electronic shutter speed of $\frac{1}{1000}$ second to the CCD driving circuit 33.

The CCD driving circuit 33 controls an output of the discharge pulses φSUB (time H) as described with reference to FIG. 4, thereby setting the above-mentioned electronic shutter speed.

When the image is magnified by manipulating the magnification changing switch 20 as described above, an electronic shutter speed is enhanced, whereby the electronic endoscope apparatus prevents the magnified image from being blurred and forms a stable and favorable moving image even when the tip of the endoscope is swung or a location to be observed pulsates.

Simultaneously, the second embodiment controls a quantity of rays emerging from the stop 25 by way of the stop driving circuit 26 on the basis of data of the input luminance signal Y by limiting a driving width of the stop 24 to a narrower variable width K at a higher magnification ratio as described above, for example, a variable width K2 at a middle magnifying point or a variable width K3 at a maximum magnifying location. Speaking concretely, a position (rotating position) of the stop blade 24A is detected with the position detector 24D and supplied to the CPU 31, which inhibits the stop 24 from being driven to a position other than stop positions k2 and k3 at the middle point or a position other than stop positions k1 and k2 at the maximum location. As a result, the second embodiment is capable of preventing response of the stop 24 from being delayed, thereby suppressing disturbance on the screen.

When the CPU 31 judges that luminance data has a value smaller than a predetermined value and an image is dark while the variable width is limited, the CPU 31 commands the CDS/AGC circuit 35 to enhance again of the video signal by a level corresponding to a difference between luminance signal data and the predetermined value Accordingly, the AGC circuit 35 amplifies the video signal, thereby preventing the brightness of the image from being lowered by limiting the variable width of the stop.

Figure 9:
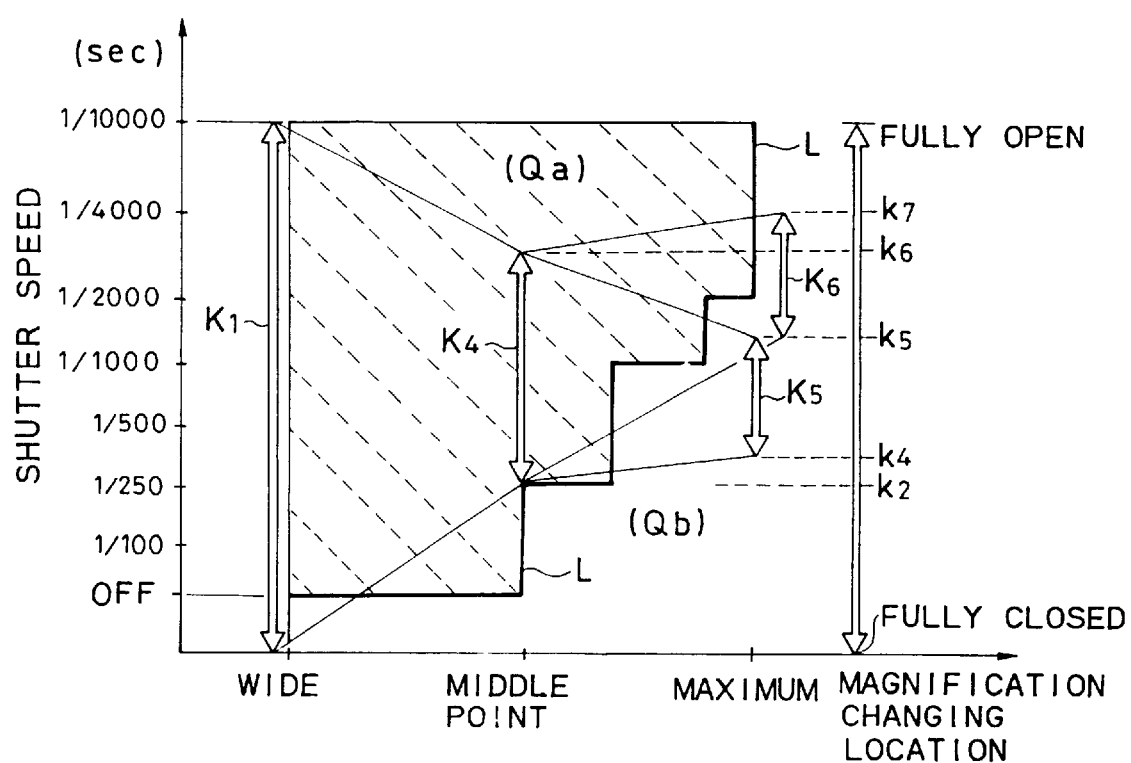
FIG. 9 is a graph showing a preferable setting range for the electronic shutter and another example of variable width of the stop in the second embodiment.

FIG. 9 shows another preferable example of preferable setting range of the electronic shutter speed and variable width of the stop mechanism, and it is preferable to set the electronic shutter speed within a region Qa on the left side of a thick line L in FIG. 9, thereby favorably preventing an image from being blurred. Accordingly, shutter speeds which can be set manually with the shutter speed setting switch 21 described above are also limited within the region Qa and shutter speeds within a region Qb cannot be set with the switch 21 in the second embodiment.

Furthermore, the limiting range of the stop 24 is narrowed gradually from the variable with K4 (stop positions from k2 to k6) at the middle point and a variable width K5 (stop positions from k4 to k5), K6 (stop positions from k5 to K7) or an optional variable width may be set at the maximum location.

The second embodiment is capable of preventing an image from being blurred when the image is picked up utilizing the magnification changing mechanism and providing a stable image having favorable brightness as described above. Furthermore, the second embodiment provides advantageously prevents an image from being darkened by limiting the variable width and always allows obtaining a constant brightness since this embodiment adjusts the gain of the image signal which the gain control circuit when predetermined brightness cannot be obtained even by the light quantity control with the stop mechanism described above.

Third Embodiment

Figure 10:
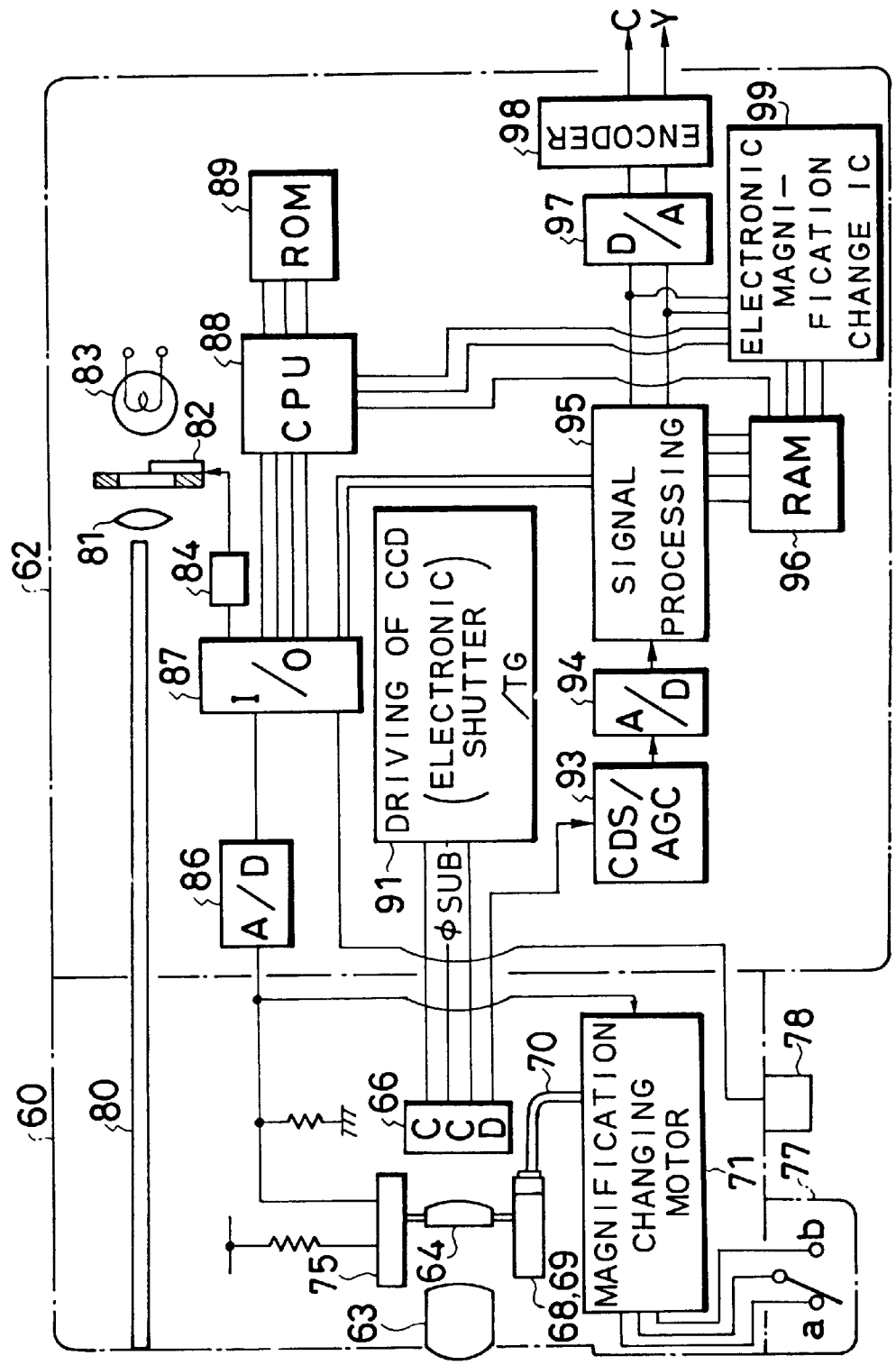
FIG. 10 is a diagram showing an overall configuration of a third embodiment of the electronic endoscope apparatus having the magnification changing function according to the present invention.

FIGS. 10 and 11 show a configuration of a third embodiment of the electronic endoscope apparatus having the magnification changing function, wherein a front lens 63 and a movable lens 64 which moves frontward and rearward are disposed in an electronic endoscope 60 shown in FIG. 10 as a vari-focal objective optical system or a zoom optical system having a variable focal length, and a CCD 66 is disposed after the movable lens 64, for example, with a prism 65 shown in FIG. 11 interposed.

FIG. 11 shows a configuration of an optical magnification changing mechanism, wherein the objective optical system comprising the movable lens 64 is disposed in a tip 60A of the electronic endoscope 60 as shown in FIG. 11. A holding member 68 for the movable lens 64 has an internally threaded portion 68A on a top thereof, a rotating drive body 69 for screwing an externally threaded portion 69A is disposed in the internally threaded portion 68A and a linear transmission member (multiply coiled spring member) 70 consisting of a multiply coiled spring member or the like is coupled with the rotating drive body 69.

The linear transmission member 70 is laid to a magnification changing motor unit 71 located at a root of a flexible inserting section of the electronic endoscope 60, and a motor 74 is connected to the linear transmission member 70 by way of gears 71A and 72B. When the motor 74 rotates, the movable lens 64 is moved frontward or rearward owing to screw coupling between the rotating drive body 69 of the linear transmission member 70 and the threaded portions 68A and 69A of the holding member 68, whereby a magnification changing operation is carried out. In the third embodiment, a viewing distance (focal length) is changed in a direction toward the far position by moving the movable lens 64 frontward or in a direction toward the near position by moving the movable lens 64 rearward.

On the other hand, an encoder 75 is attached to the holding member of the movable lens 64 to detect a magnification changing location of the movable lens 64. An output of the encoder 75 is supplied to the magnification changing motor unit 71 as shown in FIG. 10 to perform positional control on the basis of a detected current location and a target magnification changing location. The encoder 75 or a similar detecting member may be disposed in a rotating section or the like on a side of an operation unit 60B as indicated by a reference numeral 75' in FIG. 11.

In FIG. 10, a magnification changing switch 77 and a magnification changing speed switch 78 which consist of seesaw switches or the like are disposed, for example, on the operation unit of the electronic endoscope, and the magnification changing switch 77 moves the movable lens 64 in the direction toward the tele position (terminal a) and in contracting direction (terminal b). The magnification changing speed switch 78 is capable of setting a magnification changing (zoom) displacement speed selected, for example, out of three steps of a high speed (for example, on the order of 3 times as high/sec), a medium speed (for example, on the order of 2 times as high/sec) and a low speed (for example, on the order of 1.5 times as high/sec) in the third embodiment.

Furthermore, a light guide 80 is laid from the electronic endoscope 60 to a light source and a light source section of a light source-processor unit 62, and a light source lamp 83 is connected to the light guide 80 with a condenser lens 81 and a stop 82 interposed. The stop 82 is driven with a stop driving circuit 84.

An A/D converter 86 which converts an analog output from the encoder 75 into a digital signal is disposed in the light source-processor unit 62 and connected by way of an I/O unit 87 to a CPU 88 which controls circuits collectively, and a ROM 89 for storing data such as electronic shutter speed control patterns (tables) is connected to the CPU 88. The CPU 88 calculates an optical magnification changing displacement speed as described later in detail on the basis of the magnification changing location detected with the encoder 25.

Furthermore, there is disposed a CCD driving circuit 91 comprising a timing generator (TG) which performs drive control of a CCD 66 and executes electronic shutter control during a magnification changing operation while receiving a command signal from the CPU 88. Speaking concretely, the CCD driving circuit 91 is configured to be capable of setting a shutter speed, for example, of $\frac{1}{1000}$ second at maximum which is higher than that available without using the magnification changing mechanism by adjusting a discharge time in the electric charge accumulating operation of the CCD 66 on the basis of the electronic shutter control patterns stored in the ROM 89, thereby changing an electric charge accumulating time (exposure time). This electronic shutter speed control makes it possible to suppress blurring of an image which is remarkable when the image is magnified.

In order to process a video signal obtained with the CCD 66, on the other hand, there are disposed a CDS/AGC circuit 93, an A/D converter 94, a signal processing circuit 95 which generates a color difference signal C and a luminance signal Y, for example, and performs various processings such as gamma correction and contour correction, a RAM 96 which stores data processed by the signal processing circuit 95, a D/A converter 97, an encoder which processes an output to a monitor and so on.

Furthermore, an electronic magnification changing IC circuit 99 is connected to the RAM 96 to process an image for an electronic magnification change under control by the CPU 88. In the third embodiment, an electronic magnification change is carries out to further magnify an image from the tele position of art optical electronic magnification change, and an image at the tele position of the optical magnification change is stored into the RAM 96, and this image is read out as an original image and magnified. In addition, the third embodiment is configured to permit selecting whether or not this magnification changing function is to be used with a switch or the like disposed on a control panel (not shown). Furthermore, the CPU 88 detects a displacement speed during the optical magnification change and controls so as to equalize a displacement speed during the magnification change between the optical magnification change and the electronic magnification change.

Figure 12:
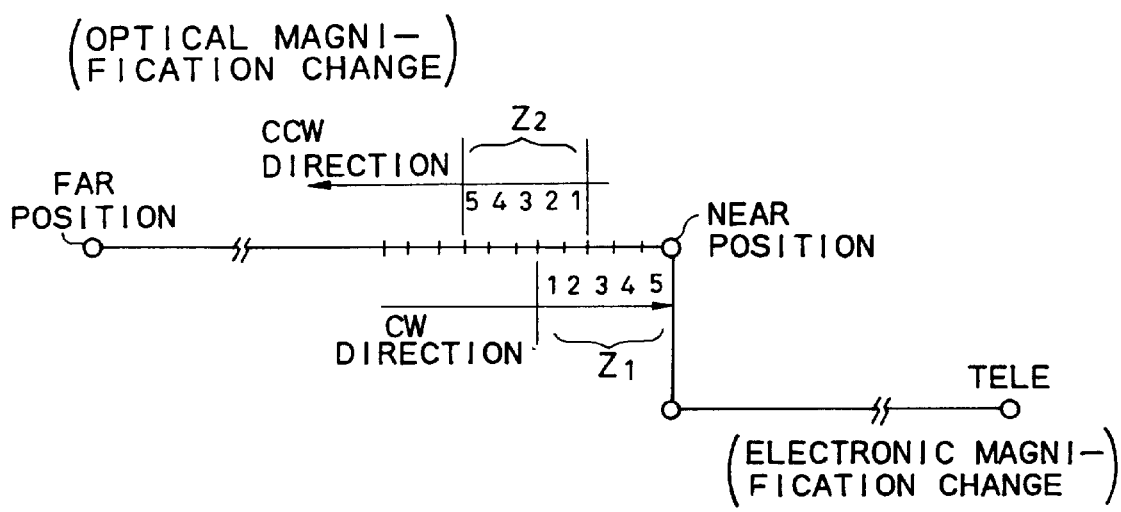
FIG. 12 is a diagram descriptive of relationship between an optical magnification change and an electronic magnification change as well as data sampling.
Figure 13:
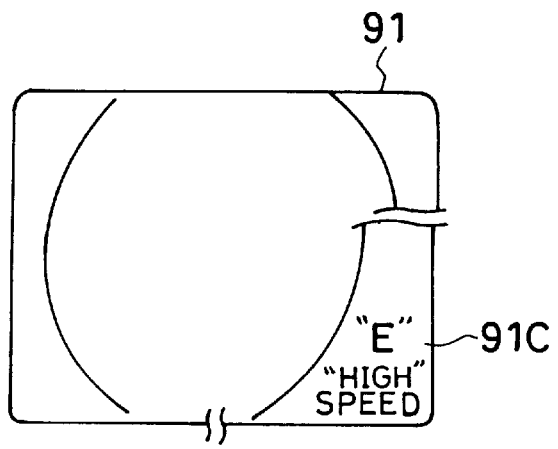
FIG. 13 is a diagram showing display of operating conditions related to a magnification change on a monitor in the third embodiment.

Speaking concretely, the magnification changing speed switch 78 set the displacement speed at three steps of a high speed, a medium speed and a low speed, but an actual driving speed is not as it is set, variable dependently on various conditions and slightly different between the magnifying direction and the contracting direction since the optical magnification changing mechanism uses a relatively long linear transmission member and the endoscope can be freely curved. In the third embodiment, the CPU 88 calculates the magnification changing speed from magnification changing location data moving during five sample counts as indicated, for example, by z1 in a CW direction toward the tele position and z2 in a CCW direction toward the far position as shown in FIG. 12, and the electronic magnification changing IC circuit 99 executes an electronic magnification changing operation at a displacement speed which is the same as the calculated displacement speed. In addition, the signal processing circuit 95 carries out not only a processing to display the image of the object to be observed but also an image processing to display whether the magnification changing speed described above and a current magnification changing operation are for the optical magnification change or the electronic magnification change, and displays "high speed," "medium speed" or "low speed" representing a magnification changing speed and O" representing the optical magnification change or "E" representing the electronic magnification change at a corner 91C of a screen, for example, as shown in FIG. 13.

Like the other embodiments, the third embodiment which has the configuration described above reads out electric charges accumulated for approximately $\frac{1}{60}$ second, for example, after fixed discharge pulses are output when the magnification changing switch 77 is not manipulated. The encoder 98 outputs the color difference signal C and the luminance signal Y by processing a read signal as a video signal, whereby an image of an interior of an object to be observed is displayed on a monitor.

When the magnification changing switch 77 is manipulated, on the other hand, the rotating drive body 69 shown in FIG. 11 is driven and rotated by the magnification changing motor unit 71 via the linear transmission member 70 and the movable lens 64 is moved frontward from the wide position, thereby magnifying an image. Simultaneously, the encoder 75 detects an optical magnification changing location (tele position) of the movable lens 64, and a value of a detected location is utilized as a control value by the magnification changing motor unit 71 and supplied as current magnification changing location data to the CPU 88 by way of the I/O unit 87. Using the optical magnification changing data, the CPU 88 calculates a magnification changing speed (magnification changing displacement speed) and sets this speed as a magnification changing speed to be used at a switching stage to the electronic magnification change.

Figure 14:
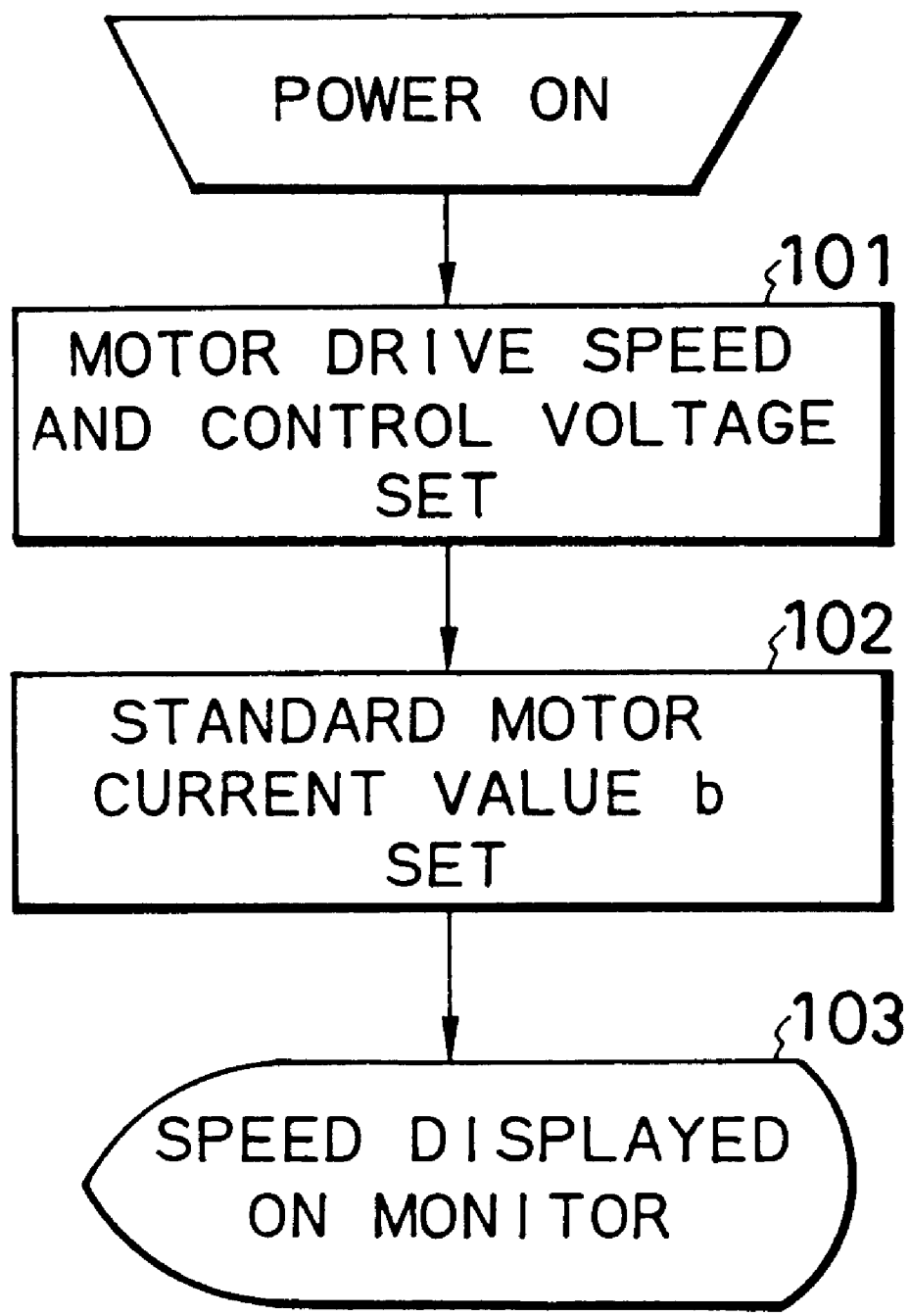
FIG. 14 is a flow chart showing a speed setting operation for an optical magnification changing motor in the third embodiment.

Now, description will be made of operations of the third embodiment mainly for setting and controlling the magnification changing speed described above. FIG. 14 shows a flow chart to set a motor speed. Upon turning on the light source, a motor driving speed control voltage which is set with the magnification changing speed switch 78, for example, the high speed, medium speed or low speed, is set at a step 101 and a standard current b for preventing motor overload, for example, a high speed=b1, a medium speed=b2 or a low speed=b2, is set at a step 102. At a step 103, a speed is displayed at the corner 91C of the monitor 91 as described with reference to FIG. 13.

Figure 15:
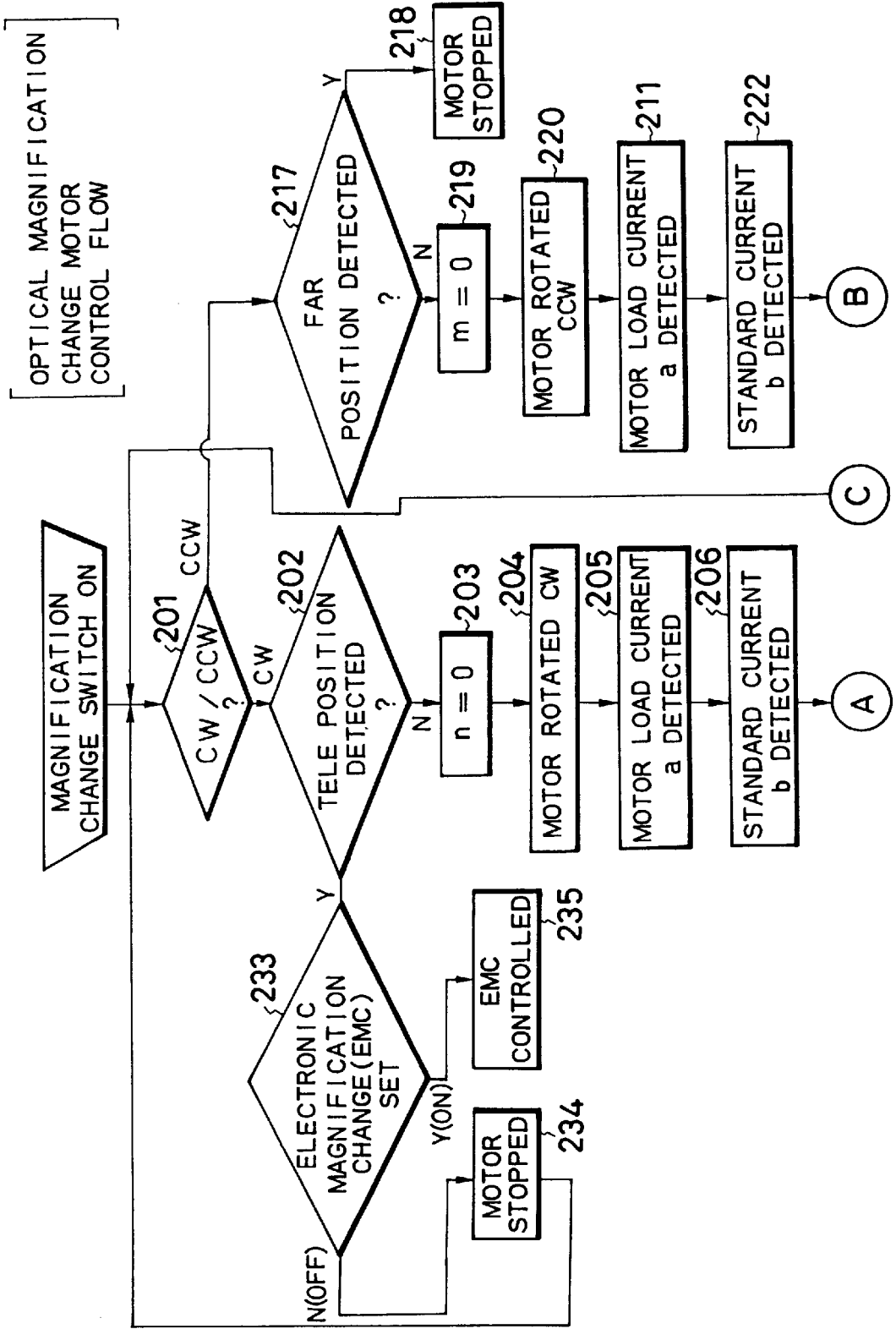
FIG. 15 is a flow chart showing control operations for the optical magnification changing motor in the third embodiment.
Figure 16:
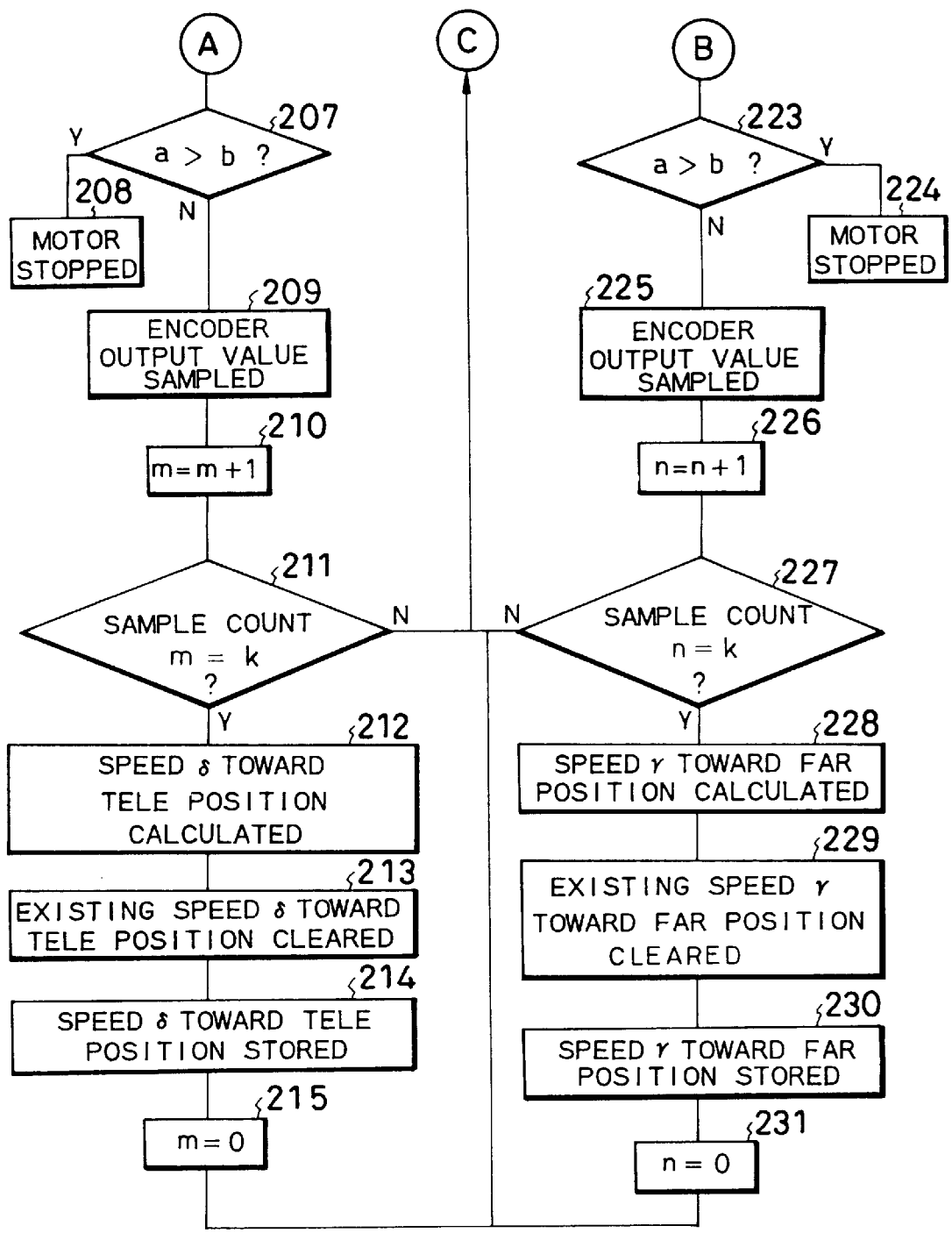
FIG. 16 is a flow chart showing control operations for the optical magnification changing motor in the third embodiment, which are subsequent to those shown in FIG. 15.

FIGS. 15 and 16 show flow charts of motor control for the optical magnification change, wherein upon depressing the magnification changing switch 77, the third embodiment judges at a step 201 whether the magnification changing switch 77 is depressed in the CW (clockwise) direction or the CCW (counterclockwise) direction. The third embodiment sets the CW direction and the CCW direction as a direction toward the tele position and a direction toward the far position (contracting direction) respectively, and when the magnification changing switch 77 is depressed in the CW direction, the third embodiment judges at a step 202 whether or not the near position is detected, in case of "N (NO"), it sets a count n at 0 for control in the reverse CCW direction at a step 203 and rotates the motor 74 in the CW direction at a step 204. 15 Then, the third embodiment detects a load current a of the motor 74 (step 205) and the standard current (b1, b2 or b3) mentioned above (step 206).

At a step 207 in FIG. 16, the third embodiment detects whether or not the load current a is higher than the standard current b (b1, b2 or b3), and in case of "Y (YES)," it stops the motor 74 to release the motor from an overloaded condition. At a next step 209, the third embodiment samples a detection value output from the encoder 75 and adds 1 to a count m (m+1) (step 210), and judges at a step 211 whether or not a sample count m reaches k (for example, k=5) and in case of m=k, the third embodiment calculates a magnification changing speed in the direction toward the tele positional step 212. Speaking concretely, the third embodiment determines a magnification changing speed δ by sampling five magnification changing locations (z1), for example, in the CW direction as shown in FIG. 12. At a step 213, the third embodiment clears (erases) an existing speed (a speed calculated for a preceding magnification change) δ and stores the magnification changing speed determined at the step 212 into the RAM 96 (step 214). At a subsequent step 215, the third embodiment resets the count m at 0 and returns to the step 201.

When the magnification changing switch 77 is depressed in the CCW direction at the step 201 shown in FIG. 15, on the other hand, the third embodiment proceeds to a step 217 to judge whether or not the far position is detected and in case of "Y," it stops the motor 74 (step 218) or in case of "N," the third embodiment sets the count m at 0 for control in the reverse CW direction and rotates the motor 74 in the CCW direction at a step 220. Operations of the third embodiment at subsequent steps 221 through 231 (FIGS. 16) are similar to those at the steps 205 through 215, where the third embodiment calculates magnification changing speed γ in the direction toward the far position, for example, on the basis of data z2 of the five magnification changing locations shown in FIG. 12 which are sampled during movement in the direction toward the far position (contracting direction) and progressively updates the speed data γ in the RAM 96.

In case of the (Y) which indicates detection of the tele position at the step 202, the third embodiment proceeds to a step 233 and judges whether or not the electronic magnification changing control (EMC) is selected and set. Speaking concretely, the third embodiment is configured to be capable of selecting whether or not an electronic magnification changing mode is to be used and stops the motor 74 (a step 234) when the electronic magnification changing mode is not to be used (N is set) or proceeds to the electronic magnification changing control (a step 235) when the electronic magnification changing mode is to be used (Y is set).

Figure 17:
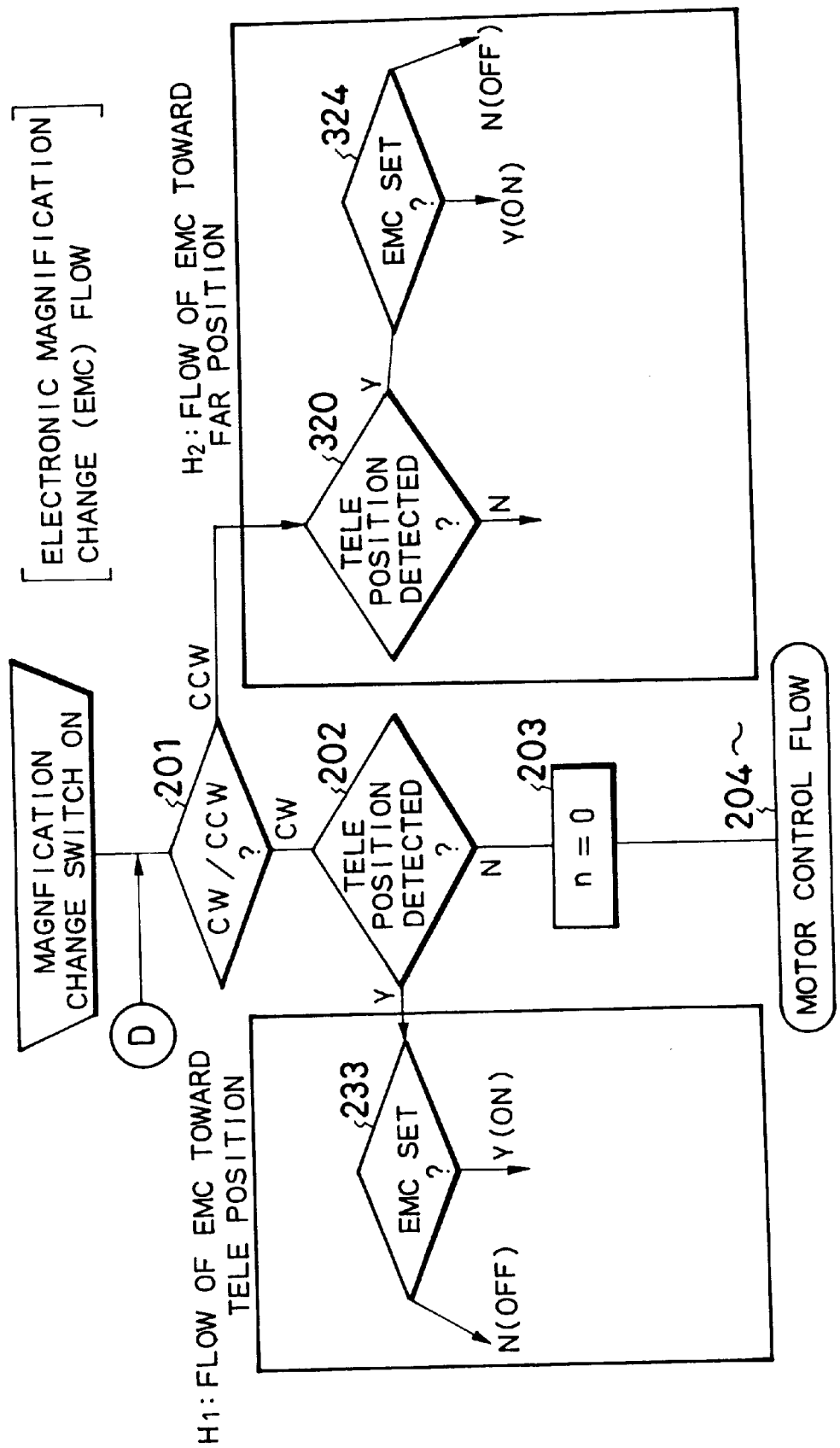
FIG. 17 is a flow chart showing electronic magnification changing control operations in the third embodiment.
Figure 18:
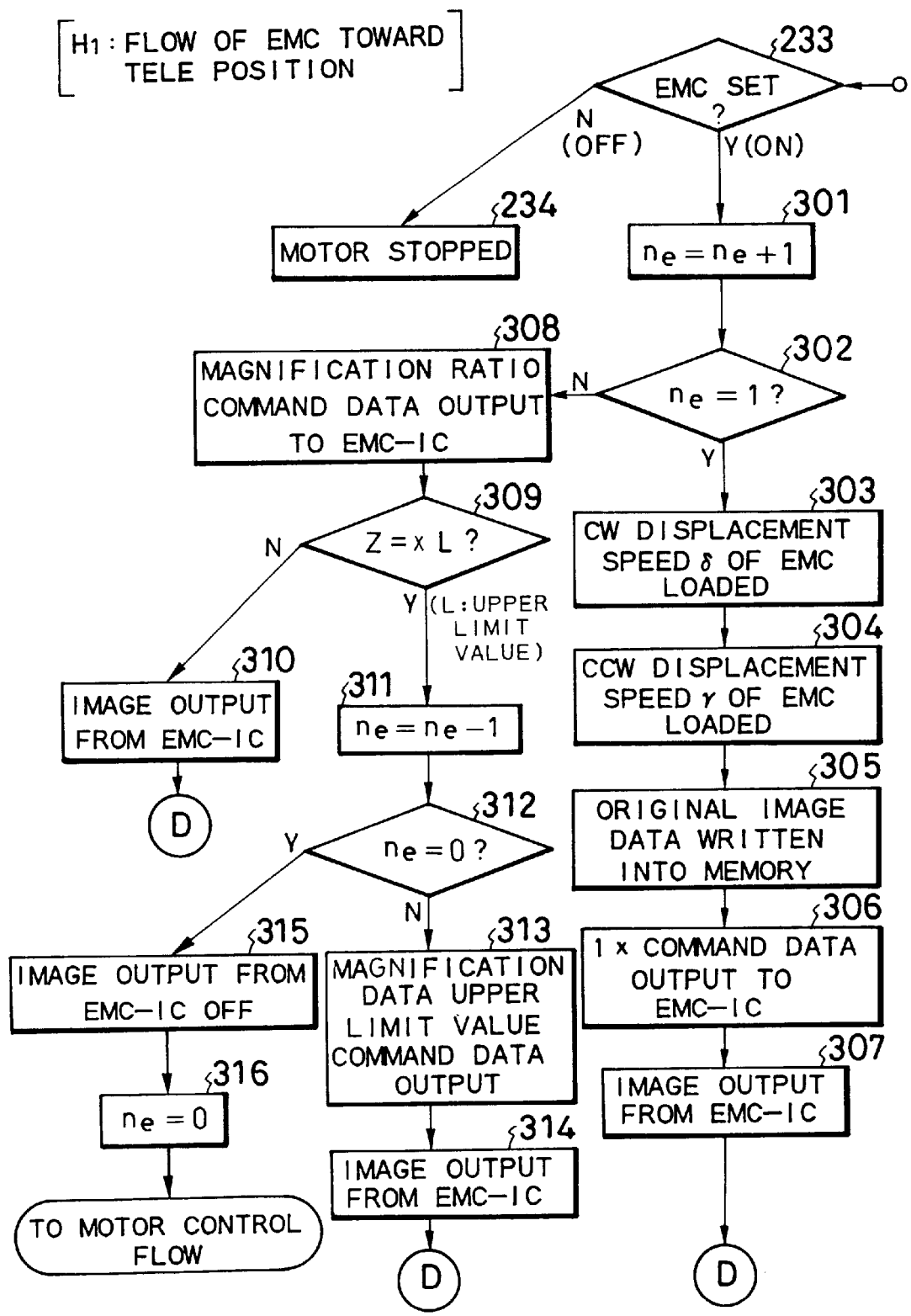
FIG. 18 is a flow chart showing electronic magnification changing operations in a magnifying direction shown in FIG. 17 in the electronic magnification changing control operations of the third embodiment.
Figure 19:
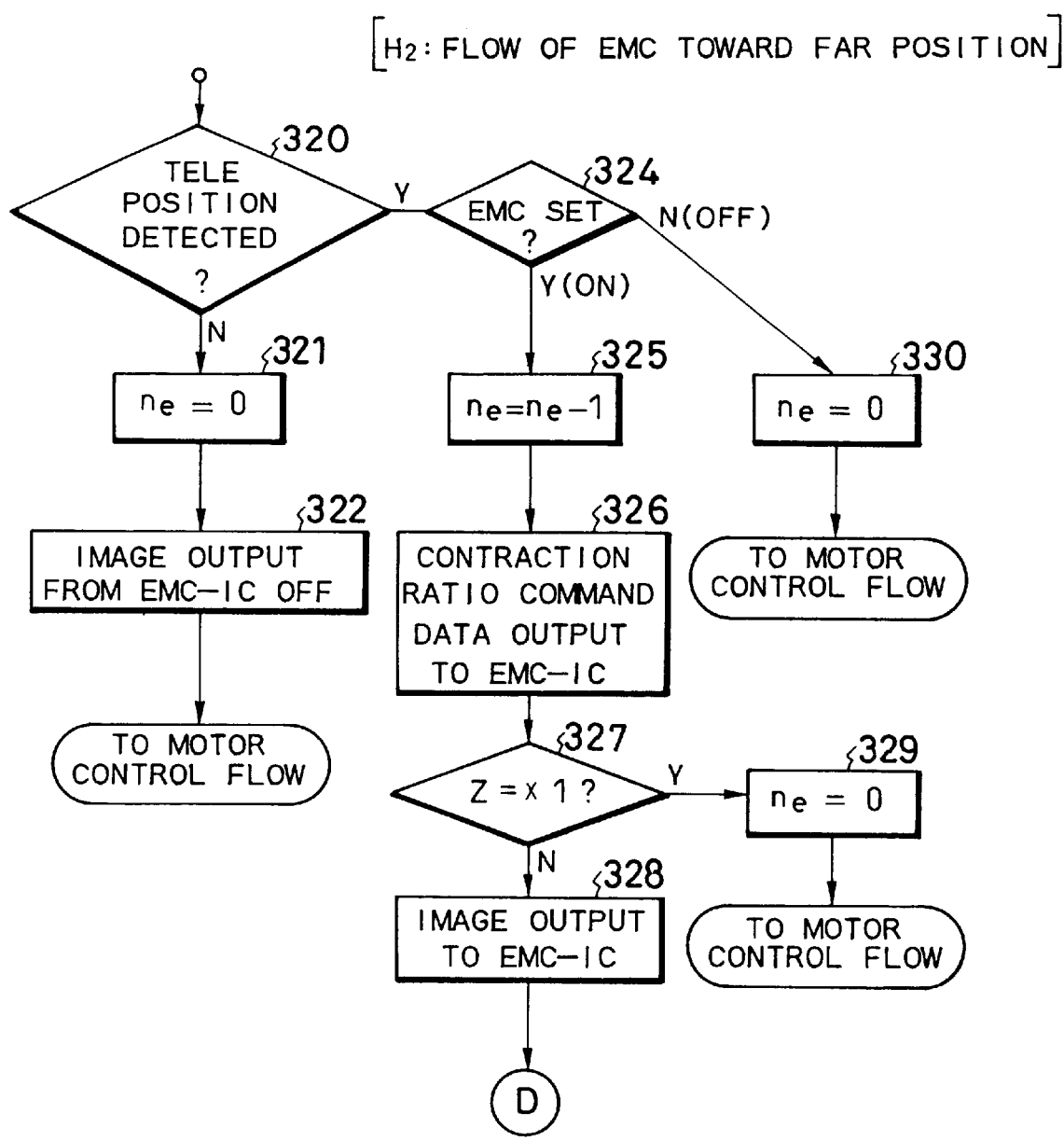
FIG. 19 is L flow chart showing electronic magnification changing operations in a wide-angle (contracting) direction shown in FIG. 17 in the electronic magnification changing control operations of the third embodiment.

FIGS. 17 through 19 show flow charts for the electronic magnification changing (EMC) control, where the third embodiment proceeds to a flow H1 for electronic magnification change toward the tele position when the tele position is detected at the step 202 as described with reference to FIG. 16 and the electronic magnification changing control is selected (on) at a step 233. Speaking concretely, the third embodiment adds 1 to a count ne (ne+1) at a step 301 and judges whether or not the count ne is 1 at a next step 302 as shown in FIG. 18.

Immediately after switching to the electronic magnification changing mode, "Y" is indicated at the step 302, and the third embodiment loads the displacement speed δ in the CW direction which is stored at the step 214 from the RAM 96 at a step 303, loads the displacement speed γ in the CCW direction which is stored at the step 230 at a step 304 and then writes an original image data into the RAM 96 (a step 305). That is, an image formed when the tele position is reached by the optical magnification change is written as the original image.

At a next step 306, the third embodiment outputs command data magnified at the same ratio as the original image to a mode register in the electronic magnification change IC circuit 99, whereby the magnification changing IC circuit 99 outputs image data magnified at the same ratio (a step 307).

When ne is not 1 at the step 302 (N), the third embodiment outputs a magnification ratio command data to the mode register in the electronic magnification changing IC circuit 99 (a step 308) and proceeds to a next step 309. At the step 309, the third embodiment detects whether or not an electronic magnification ratio Z has reached an upper limit value (Z=×L), outputs image data magnified at a commanded ratio from 20 the electronic magnification changing IC circuit 99 (a step 310) when the upper Limits value has not been reached and returns to the initial step 201. When the magnification changing switch 77 is depressed continuously in the CW direction, the third embodiment sequentially outputs and displays images magnified at higher ratios at the step 310 while changing the images at the speed δ read at the step 303. When the medium speed is selected, for example, the images are displayed at the medium speed or an actual magnification changing speed in the vicinity of the medium speed (for example, a speed around 2 second/sec).

When the magnification ratio Z has reached the upper limit value at the step 309, the third embodiment calculates ne=ne−1 (a step 311), confirms ne is not 0 (N) at a next step 312 and then outputs magnification ratio upper limit command data to the circuit 99 (a step 313), thereby allowing the electronic magnification changing IC circuit 99 to repeatedly output images which are magnified at a maximum ratio. In case of ne=0 (Y) at the step 312 which indicates release of the magnification changing switch 77 from depression in the CW direction immediately after start of the electronic magnification changing control, the third embodiment turns off the image output from the electronic magnification changing IC circuit 99 (a step 315), sets ne at 0 once again and proceeds to a motor control flow.

When the magnification changing switch 77 is depressed in the CW direction during execution of the electronic magnification changing control, the third embodiments proceeds from the step 201 shown in FIG. 17 to an electronic magnification changing flow H2 in the CCW direction toward the far position. Speaking concretely, the third embodiment judges whether or not the tele position of the optical magnification change is detected at a step 320, executes n−0 (a step 321) in case of "N" which indicates that the electronic magnification is possible, then turns off the image output from the electronic magnification change IC circuit 99 at a step 322 and proceeds to the motor control flow.

When the tele position is detected at the step 320, on the other hand, the third embodiment judges whether the electronic magnification change is set on or off at a step 324, calculates ne=ne−1 (a step 325) when the electronic magnification change is set on (Y) and outputs contraction ratio command data to the mode register in the electronic magnification changing IC circuit 99. Then, the third embodiment judges whether or not the electronic magnification ratio Z has reached a lower limit value (Z=×1 which is equal to the maximum value for the optical magnification change) at a step 327 and in case of "N," the third embodiment outputs an image contracted at a commanded ratio from the electronic magnification changing IC circuit 99 (a step 328). When the magnification changing switch 77 is depressed continuously in the CCW direction, the third embodiment sequentially outputs and displays images which are contracted (magnified at lower ratios) while changing the images at the magnification changing speed γ read at the step 304.

In case of "Y" which indicates arrival to a lower limit value of the electronic magnification change at the step 327, on the other hand, the third embodiment calculates ne=0 at a step 329 and proceeds to the motor control flow. Also when the electronic magnification change is set off (N) at the step 324, the third embodiment calculates ne=0 at a step 330 and proceeds to the motor control flow.

The third embodiment allows a magnification changing function to expand a magnification changing region further from the tele position of the optical magnification change by manipulating the magnification changing switch 70 as described above, and performs magnification change and displacement smoothly at the same speed during switching between both the magnification changing functions, thereby executing the optical magnification change and the electronic magnification change with no feeling of strangeness. Since "O" and "E" are displayed on the monitor 91 during the optical magnification change and the electronic magnification change respectively as described with reference to FIG. 13, the third embodiment permits recognizing whether the magnification change is carried out in either mode.

Though the electronic magnification change function is used to expand the magnification changing region from the tele position of the optical magnification change in the embodiment described above, it is possible to use the electronic magnification change function in a direction to narrow the magnification change region from the wide end of the optical magnification change.

The third embodiment is capable of enhancing a magnifying ratio by combining the optical magnification change function with the electronic magnification change function as described above and smoothly switching one of the magnification change function to the other during a magnification changing operation. Even when a driving force of a motor is transmitted using a linear transmission member in particular, the third embodiment is capable of matching magnification changing displacement speeds with precision between the two magnification change functions.

What is claimed is:

1. An electronic endoscope apparatus having a magnification changing function, comprising:

an optical magnification changing mechanism which is capable of optically magnifying an image to be observed with an objective optical system;

a solid-state image pickup device which picks up an image of an object to be observed using rays incident from said objective optical system; and an electronic shutter control circuit, which controls an electric charge accumulating time of the solid-state image pickup device and sets a high shutter speed which is shorter than an exposure time while the magnification changing mechanism is not operating during an operation of said optical magnification changing mechanism;

wherein various kinds of patterns which provide higher electronic shutter speeds as an image magnification ratio is enhanced by said optical magnification changing mechanism are stored in a memory and the electronic shutter speed is controlled by reading data of a pattern selected from the memory.

2. The electronic endoscope apparatus having a magnification changing function according to claim 1, wherein said optical magnification changing mechanism comprises a motor and a linear transmission member which transmits a driving force of the motor, and a movable lens is moved to change a magnification with the driving force from the motor disposed at a distant location.

3. The electronic endoscope apparatus having a magnification changing function according to claim 1, wherein a shutter speed set by said electronic shutter control circuit is displayed on a monitor.

4. An electronic endoscope apparatus having a magnification changing functions comprising:

an optical magnification changing mechanism which is optically magnifying an image to be observed with an objective optical system; a solid-state image pickup device which picks up an image of an object to be observed using rays incident from said objective optical system;

an electronic shutter control circuit which controls an electric charge accumulating time of the solid-state image pickup device and sets a high shutter speed which is shorter than an exposure time while the magnification changing mechanism is not operating during operation of said optical magnification changing mechanism;

a stop mechanism which varies and controls rays output from a light source with a stop member; and a control circuit which limits a variable width of said stop mechanism to a predetermined width as said electronic shutter speed is enhanced while said optical magnification changing mechanism is operative.

5. The electronic endoscope apparatus having a magnification changing function according to claim 4, wherein said electronic endoscope apparatus comprises a gain control circuit which controls a gain of an image signal output from said solid-state image pickup device and image brightness is maintained constant by adjusting the gain of the image signal with said gain control circuit when predetermined brightness is not obtained even by light quantity control with said stop mechanism.

6. An electronic endoscope apparatus having a magnification changing function, comprising:

an optical magnification changing mechanism which is capable of optically magnifying an image to be observed with an objective optical system;

a solid-state image pickup device which picks up the image to be observed using rays incident from said objective optical system;

an electronic magnification changing circuit which processes an image signal obtained with the solid-state image pickup device and forms a magnified image and a contracted image of an image formed at an operation end of the electronic magnification change; and a magnification change speed control circuit which detects a displacement speed of the magnification change in said optical magnification changing mechanism and controls to match a magnification changing displacement speed of the electronic magnification change operation with a magnification changing displacement speed of an electronic magnification change operation at a switching point;

wherein said optical magnification changing mechanism comprises a movable lens which is movably built in to change a magnification and a detector which detects a magnification changing location of the movable lens, and said magnification change speed control circuit determines a displacement speed from magnification change location data of said movable lens sampled at predetermined counts.

7. The electronic endoscope apparatus having a magnification changing function according to claim 6, wherein said optical magnification changing operation, said electronic magnification changing operation and switching between both the operations are controlled with a magnification changing switch.

8. The electronic endoscope apparatus having a magnification changing function according to claim 6, wherein a displacement speed detected with said magnification changing speed control circuit is displayed on a monitor.

9. The electronic endoscope apparatus having a magnification changing function according to claim 7, wherein an image which is currently formed is optically magnified or electronically magnified and is displayed on a monitor.

* * * * *